United States Patent
Tsakas et al.

(10) Patent No.: US 11,246,802 B2
(45) Date of Patent: Feb. 15, 2022

(54) CONTAINER AND CLOSURE

(71) Applicant: EULYSIS UK LIMITED, Roslin Midlothian (GB)

(72) Inventors: Spyridon Edouard Tsakas, Hudson, MA (US); Spyridon Christos Tsakas, Athens (GR)

( * ) Notice: Subject to any disclaimer, the term of this patent is extended or adjusted under 35 U.S.C. 154(b) by 1186 days.

(21) Appl. No.: 15/509,701

(22) PCT Filed: Sep. 8, 2015

(86) PCT No.: PCT/GB2015/052597
§ 371 (c)(1),
(2) Date: Mar. 8, 2017

(87) PCT Pub. No.: WO2016/038357
PCT Pub. Date: Mar. 17, 2016

(65) Prior Publication Data
US 2017/0258683 A1    Sep. 14, 2017

(30) Foreign Application Priority Data

Sep. 8, 2014   (GB) .................................... 1415869

(51) Int. Cl.
*A61J 1/20*    (2006.01)
*B01L 3/00*   (2006.01)
(Continued)

(52) U.S. Cl.
CPC .......... *A61J 1/2072* (2015.05); *A61J 1/1406* (2013.01); *A61J 1/1412* (2013.01); *A61J 1/2027* (2015.05);
(Continued)

(58) Field of Classification Search
CPC ...... A61J 1/2072; A61J 1/2075; A61J 1/2068; A61J 1/2027; A61J 1/1406; A61J 1/1412;
(Continued)

(56) References Cited

U.S. PATENT DOCUMENTS 4,781,679 A  * 11/1988  Larkin .................. A61J 1/2089
                                                             604/413
4,858,760 A    8/1989  Di Sturco
(Continued)

FOREIGN PATENT DOCUMENTS

CN        103381131       11/2013
DE        697 19 951       1/2004
(Continued)

OTHER PUBLICATIONS

International Search issued in PCT/GB2015/052597, dated Feb. 11, 2016 (8 pages).
(Continued)

*Primary Examiner* — Brandy S Lee
*Assistant Examiner* — Nidah M Hussain
(74) *Attorney, Agent, or Firm* — Fay Sharpe LLP

(57) ABSTRACT

A closure for dispensing one or more active agents into a container comprises a sealed or sealable chamber having a breakable wall and a hollow piston slidably mounted in a piston guide. Said hollow piston comprises an outer wall having an end in the chamber and at least one ventilation aperture. Said end has a cutting formation. Said hollow piston is slidable in the piston guide between a ventilation position in which the at least one ventilation aperture allows ventilation of the chamber and a sealed position in which the at least one ventilation aperture is sealed to prevent ventilation of the chamber and a deployed position in which the cutting formation has broken through at least a portion of the breakable wall. The outer wall has a retaining formation which engages with the piston guide to releasably resist sliding of the hollow piston between the ventilation position and the sealed position and the deployed position. The hollow piston may have an outer wall, and said outer wall has an end within the chamber, facing the breakable wall, (Continued)

wherein the cutting end has a first edge having a cutting formation and a gap in said cutting formation.

14 Claims, 6 Drawing Sheets

(51) Int. Cl.
| | |
|---|---|
| *B65B 29/10* | (2006.01) |
| *B65D 51/28* | (2006.01) |
| *B65D 51/24* | (2006.01) |
| *B65D 51/00* | (2006.01) |
| *A61J 1/14* | (2006.01) |
| *A61K 9/00* | (2006.01) |
| *A61K 9/08* | (2006.01) |
| *A61K 38/00* | (2006.01) |
| *A61K 38/43* | (2006.01) |
| *A61K 39/00* | (2006.01) |
| *A61M 11/00* | (2006.01) |
| *B65B 7/28* | (2006.01) |
| *B65B 55/02* | (2006.01) |
| *B65B 63/08* | (2006.01) |

(52) U.S. Cl.
CPC ........... *A61J 1/2075* (2015.05); *A61J 1/2093* (2013.01); *A61J 1/2096* (2013.01); *A61K 9/0019* (2013.01); *A61K 9/08* (2013.01); *A61K 38/00* (2013.01); *A61K 38/43* (2013.01); *A61K 39/00* (2013.01); *A61M 11/00* (2013.01); *B01L 3/502* (2013.01); *B01L 3/523* (2013.01); *B65B 7/28* (2013.01); *B65B 29/10* (2013.01); *B65B 55/02* (2013.01); *B65B 63/08* (2013.01); *B65D 51/002* (2013.01); *B65D 51/241* (2013.01); *B65D 51/2814* (2013.01); *B65D 51/2835* (2013.01); *A61J 1/1425* (2015.05); *A61J 1/1431* (2015.05); *B01L 2200/141* (2013.01); *B01L 2300/042* (2013.01); *B01L 2300/043* (2013.01); *B01L 2300/044* (2013.01); *B01L 2300/047* (2013.01); *B01L 2300/048* (2013.01); *B01L 2300/0672* (2013.01)

(58) Field of Classification Search
CPC ...... A61J 1/2096; A61J 1/2093; A61J 1/2089; A61J 1/2006; A61J 1/201; B65B 7/28; B65D 51/002; B65D 51/2814; B65D 51/2835; B01L 2300/042; B01L 2300/043; B01L 2300/044; B01L 2300/048; B01L 2300/0672; A61M 2039/0036; A61M 2039/205
USPC .......................................................... 604/93
See application file for complete search history.

(56) References Cited

U.S. PATENT DOCUMENTS

| | | | | |
|---|---|---|---|---|
| 4,982,875 | A * | 1/1991 | Pozzi | B65D 51/285 222/83 |
| 5,522,155 | A * | 6/1996 | Jones | B65D 51/241 34/286 |
| 5,931,828 | A | 8/1999 | Durkee | |
| 6,387,073 | B1 * | 5/2002 | Weiler | A61J 1/2093 206/222 |
| 8,215,481 | B1 | 7/2012 | Knickerbocker | |
| 8,839,982 | B1 * | 9/2014 | Anderson | B65D 51/2835 206/222 |
| 2001/0009151 | A1 * | 7/2001 | Hochrainer | B05B 7/24 128/200.14 |
| 2006/0108314 | A1 * | 5/2006 | Cho | B65D 51/285 215/228 |
| 2006/0251771 | A1 * | 11/2006 | Yokota | B65D 51/2835 426/115 |
| 2007/0193894 | A1 | 8/2007 | Macken et al. | |
| 2008/0125704 | A1 * | 5/2008 | Anderson | A61J 1/18 604/87 |
| 2010/0111772 | A1 | 5/2010 | Hartofelis | |
| 2011/0073501 | A1 * | 3/2011 | Wu | A61J 1/065 206/219 |

FOREIGN PATENT DOCUMENTS

| | | |
|---|---|---|
| EP | 0 217 425 | 4/1987 |
| EP | 0 344 849 | 12/1989 |
| FR | 2245947 | 4/1975 |
| GB | 676492 | 7/1952 |
| GB | 1026138 | 4/1966 |
| GB | 2 485 254 | 5/2012 |
| JP | 2007-076738 A | 3/2007 |
| WO | WO 97/48492 | 12/1997 |
| WO | WO 02/36065 | 5/2002 |
| WO | WO 2008/036889 | 3/2008 |
| WO | WO 2012/153206 A1 | 11/2012 |
| WO | WO 2013/026995 | 2/2013 |

OTHER PUBLICATIONS

Written Opinion of the International Searching Authority issued in PCT/GB2015/052597, dated Feb. 11, 2016 (14 pages).

* cited by examiner

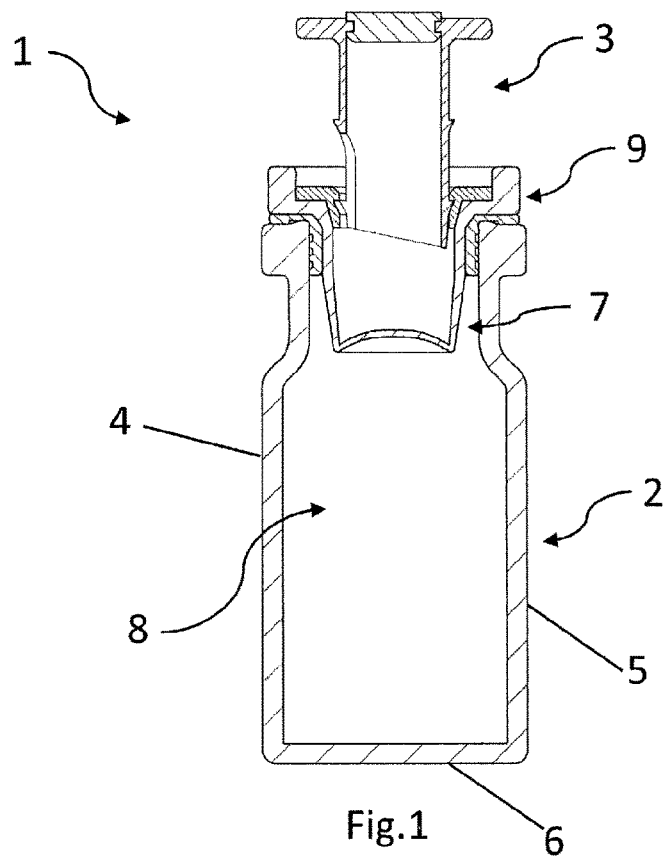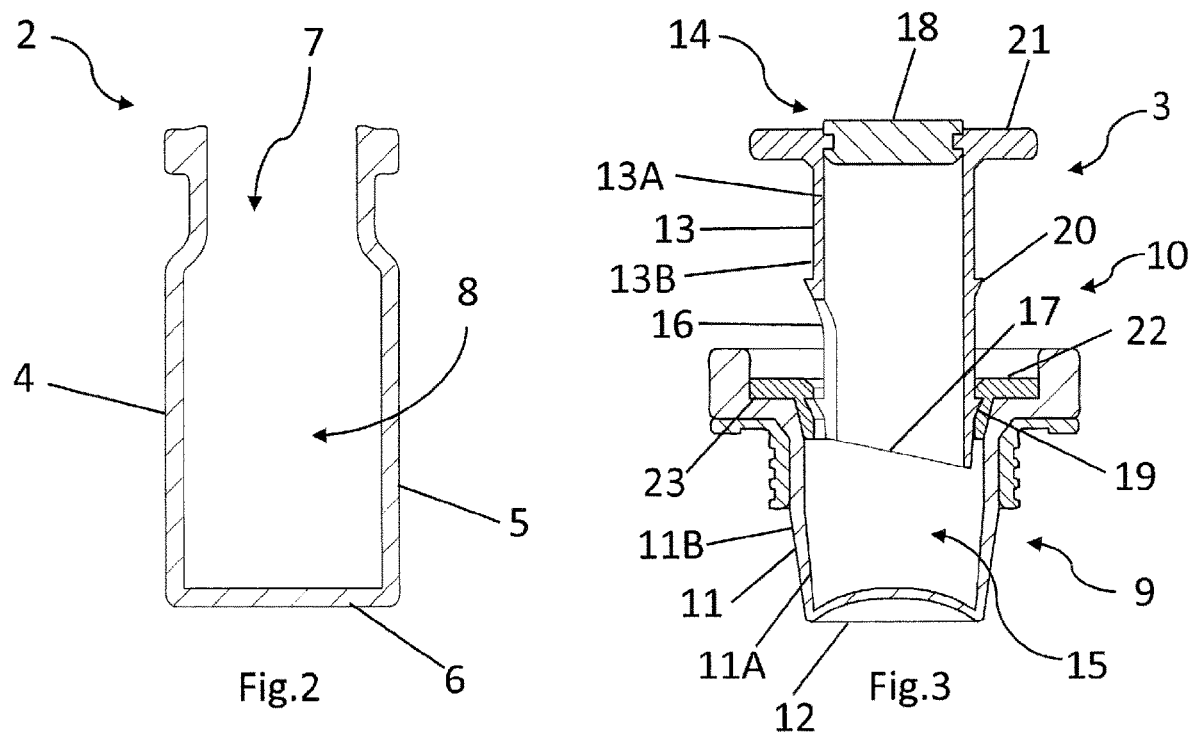

CONTAINER AND CLOSURE

This application is the U.S. national phase of International Application No. PCT/GB2015/052597 filed 8 Sep. 2015 which designated the U.S. and claims priority to GB Patent Application No. 1415869.5 filed 8 Sep. 2014, the entire contents of each of which are hereby incorporated by reference.

FIELD OF THE INVENTION

The invention relates to the field of containers with a dry active agent, a liquid diluent and a mechanism for combining the two before use, as well as claims for closures for such containers, and methods of manufacturing such containers and closures retaining dry active agents and liquid diluents.

BACKGROUND TO THE INVENTION

In the fields of biochemistry and medicine it is common to use active biological species in solution. Such active agents, while stable in vivo, are often found to be unstable when in solution in vitro. In such cases, it is preferable to store the active agents separately from any solvent. Dry agents may be recombined with a diluent immediately before use such that active properties do not have time to degrade. Examples of such active biological agents include proteins, enzymes, nucleic acid sequences and vaccines, which are used medicinally as, for example, oncology treatments, antibiotics, treatments for human immunodeficiency virus (HIV), or as dermatological preparations.

One method of storing such active agents safely in vitro is lyophilisation, where the sample in solution is frozen and then heated in vacuum such that the solvent sublimes. The structures of any active agents are preserved in the lyophilised state and the active agents may be stored separately from the diluent.

When active agents and diluent are stored in separate containers and then recombined prior to medicinal use, there is then a danger of contamination of the medicament. In order to avoid contamination, time-consuming recombination processes are then required. Such processes are wasteful, since two containers and two sets of packaging are required for the preparation of one medicament.

Vials and vial closures which can be used to store diluent and active agents respectively, separated by a frangible seal, are known. These provide a lower risk of contamination and are more environmentally friendly. However, there are practical and technical problems with the design such that, for example, the frangible seal may be broken during transport and storage or when mishandled by a medical practitioner. Accordingly, it is one object of the invention to provide a container and closure for safer storage and transport of active agents and diluent.

Known vials and vial closures generally require the use of a syringe to extract the recombined contents, limiting their range of use to relatively sterile environments. Some aspects of the invention aim to provide a container and closure for storage and recombination of active agents and diluent for use when sterilised syringes are either unavailable or unnecessary.

The manufacturing process of known vials and vial closures can be complex and is not suited to large scale mechanisation. Some aspects of the invention address the problem of providing an easily mechanised method of manufacturing containers and closures for storing active agents and diluents.

SUMMARY OF THE INVENTION

A first aspect of the invention provides a closure for dispensing one or more active agents into a container, the closure comprising: a sealed or sealable chamber having a breakable wall, and a hollow piston slidably mounted in a piston guide, said hollow piston comprising an outer wall, said outer wall having an end in the chamber and at least one ventilation aperture, said end having a cutting formation, said hollow piston being slidable in the piston guide between a ventilation position in which the at least one ventilation aperture allows ventilation of the chamber and a sealed position in which the at least one ventilation aperture is sealed to prevent ventilation of the chamber and a deployed position in which the cutting formation has broken through at least a portion of the breakable wall. Typically, the outer wall has a retaining formation which engages with the piston guide to releasably resist sliding of the hollow piston between the ventilation position and the sealed position and the deployed position.

It may be that the piston guide is able to releasably resist sliding of the hollow piston between the ventilation position and the sealed position and between the sealed position and the deployed position. Alternatively, it may be that the piston guide is able to releasably retain the hollow piston in the ventilation position and/or in the sealed position and/or in the deployed position.

Typically, the piston guide comprises a locating formation engageable with the retaining formation of the outer wall. For example, the locating formation may comprise a groove and the retaining formation may comprise a cooperating ridge. Alternatively, the retaining formation may comprise a groove and the locating formation may comprise a cooperating ridge. In some embodiments, the locating formation comprises at least one flanged edge portion engageable with an external surface of the outer wall. In other embodiments, retaining formation comprises at least one flanged edge portion able to engage with an internal surface of the closure. In other embodiments, the locating and retaining formations may comprise alternative mechanical, electronic or magnetic arrangements configured to releasably retain the hollow piston in the ventilation position and/or in the sealed position and/or in the deployed position.

Typically, the outer wall of the hollow piston comprises at least one ventilation aperture through which the chamber is in fluid communication with the surroundings of the closure when the hollow piston is in the ventilation position. Therefore, fluids such as gases or liquids may pass between the chamber and the surroundings through the ventilation aperture when the hollow piston is in the ventilation position. The piston guide is able to releasably resist sliding of the hollow piston between the ventilation position and the sealed position. Typically, the piston guide, therefore, acts to releasably retain the hollow piston in the ventilation position. Typically, the hollow piston is manually slidable from the ventilation position to the sealed position. The piston guide releasably resists sliding of the hollow piston from the ventilation position to the sealed position until a force greater than a threshold force is applied manually to the hollow piston when sliding is then permitted.

Typically, sliding of the hollow piston from the ventilation position to the sealed position results in the at least one ventilation aperture being sealed from the surroundings such that the chamber is no longer in fluid communication with said surroundings (and so is sealed). Therefore, fluids such as gases or liquids may not pass between the chamber and the surroundings through the ventilation aperture when the hollow piston is in the sealed position. Typically, the hollow piston is also manually slidable from the sealed position to the deployed position. The piston guide, typically, releasably resists sliding of the hollow piston from the sealed position to the deployed position until a force greater than a threshold force is applied manually to the hollow piston when sliding is permitted.

Typically, in the deployed position, at least a portion of the hollow piston extends beyond the breakable wall. It may be that, in the deployed position, the cutting formation of the outer wall cuts a hole in the breakable wall such that a portion of the breakable wall is completely detached. Typically, however, in manually sliding the hollow piston from the default position to the deployed position, only the cutting formation cuts through only a portion of the breakable wall. It may be that a gap is provided in the cutting formation. The breakable wall may, therefore, not be cut in an area proximate the gap in the cutting formation. The cut portion of the breakable wall may, therefore, remain hingedly attached to the closure when the hollow piston is in the deployed position. Said gap in the cutting formation may be formed by the at least one ventilation aperture. Therefore the breakable wall may not be broken in an area proximate the at least one ventilation aperture when the hollow piston is in the deployed position. Therefore, in such embodiments, the at least one ventilation aperture performs two functions by both permitting passage of gases or liquids between the chamber and the surroundings when the hollow piston is in the ventilation position and also by providing a gap in the cutting position preventing an area of the breakable wall being cut when sliding the hollow piston from the default position to the deployed position, while retaining the mechanical strength and integrity of the hollow piston.

Alternatively, the breakable wall may not be broken in an area proximate the gap in the cutting formation when the hollow piston is in the deployed position.

The hollow piston may be slidable in only one axial direction. For example, the hollow piston is typically slidable from the ventilation position to the sealed position and from the sealed position to the deployed position, but the hollow piston is not typically slidable from the deployed position to the sealed position or from the sealed position to the ventilation position. The outer wall of the hollow piston and the piston guide may together form a ratchet. This ensures that, once the chamber has been sealed, or once the breakable wall has been cut, the contents of the container cannot be exposed to the surroundings again, which could lead to contamination. The piston guide therefore ensures safer transport and storage of the closure or of any container comprising the closure.

A second aspect of the invention provides a closure for dispensing one or more active agents into a container, the closure comprising: a sealed or sealable chamber having a breakable wall, a hollow piston slidably mounted in a piston guide, said hollow piston comprising an outer wall, and said outer wall having an end in the chamber, facing the breakable wall, wherein the said end has a cutting formation and a gap in said cutting formation.

Typically, the hollow piston is slidable from a default position in which the said end is within the chamber to break through the breakable wall such that a portion of the outer wall extends through the breakable wall but not in an area of said breakable wall proximate the gap in the cutting formation.

Therefore, the hollow piston is slidable from a default position (in which the cutting formation faces the unbroken breakable wall), in which said end of the piston is within the chamber, to break through the breakable wall such that a portion of the outer wall extends through the breakable wall, but not in an area of said breakable wall proximate the gap in the cutting formation. Typically, the breakable wall is not broken through in an area proximate the gap in the cutting formation. The breakable wall may, therefore, not be detached fully from the closure when the hollow piston breaks therethrough. Typically, the breakable wall remains hingedly attached to the closure once the hollow piston has broken through the breakable wall. The gap in the cutting formation may therefore define a hinge region of the breakable wall, once broken. The gap may be a location around the periphery of the end of the outer wall where the end of the outer wall is recessed. The cutting formation may extend around the rest of the end of the outer wall. The end of the outer wall (and the cutting formation) may protrude further the breakable wall at the side of the outer wall opposite the gap than adjacent the gap (to facilitate breaking of the breakable wall). The end of the outer wall of the prism may slope longitudinally (and extend further parallel to the axis of the hollow piston) away from the gap.

The chamber may retain one or more active agents. The breakable wall may form a wall of the chamber. The hollow piston may in part define the chamber. The breakable wall may retain the one or more active agents within the chamber when the hollow piston is in the default position. Typically, the one or more active agents are retained within the hollow piston when the hollow piston is in the default position. It may be that the hollow piston seals the chamber from the surroundings of the closure when the hollow piston is in the default position. Typically, the hollow piston and the breakable wall together form a sealed chamber around the one or more active agents when the hollow piston is in the default position and the breakable wall is unbroken.

Typically, in the default position, the said end of the outer wall of the hollow piston is retained within the chamber. Typically, in the default position, the cutting formation of the hollow piston is adjacent the breakable wall. The hollow piston may be manually slidable from the default position to break through the breakable wall. The outer wall of the hollow piston may be aligned substantially parallel to a longitudinal axis of the hollow piston, the longitudinal axis being substantially perpendicular to the breakable wall. The gap in the cutting formation typically also extends away from the first edge, defining a recess in the outer wall of the hollow piston.

The outer wall of the hollow piston may extend from a top surface of the closure. It may be that the outer wall of the hollow piston is integrally formed from said top of the closure. The hollow piston may be manually slidable by pressing down on the top surface of the closure.

A third aspect of the invention provides a container and a closure according to the first aspect of the invention for dispensing one or more active agents into said container, wherein the closure is retained within an opening of the container. A fourth aspect of the invention provides a container and a closure according to the second aspect of the invention for dispensing one or more active agents into said container, wherein the closure is retained within an opening of the container. In each of the third and fourth aspects, typically the closure provides a seal for the opening of said container. The closure may seal the opening of said container by means of an interference fit within the opening.

Typically, once the breakable wall has been broken, a portion of the hollow piston extends beyond the breakable wall. Typically, in manually sliding the hollow piston from the default position to break through the breakable wall, at least a portion of the cutting formation breaks through at least a portion of the breakable wall, thereby breaking a seal around the sealed or sealable chamber. It may be that sliding the hollow piston to break through a portion of the breakable wall brings an internal chamber of the container into fluid communication with the chamber of the closure.

The chamber may retain one or more active agents. The container may retain liquid diluent. Typically, when in use, a liquid diluent is provided within an internal chamber of the container and one or more active agents are retained within the chamber of the closure. The breakable wall may therefore form a seal between the one or more active agents and the diluent. The one or more active agents may, therefore, be kept dry and sterile. Breaking through at least a portion of the breakable wall by sliding the hollow piston from the default position may permit at least some of the one or more active agents retained within the chamber of the closure to fall out of or otherwise exit the chamber into the container. Typically, breaking through a portion of the breakable wall by sliding the hollow piston from the default position thereby permits at least some of the one or more active agents retained within the chamber to mix with the diluent provided within the container to form a solution.

It may be that at least one of the one or more active agents comprises a biologic agent. Typically, at least one of the one or more active agents comprises an agent from the following group: a protein, an enzyme, a nucleic acid sequence, a vaccine or an antibiotic. It may be that the one or more active agents are provided in the form of a cake or tablet of lyophilised active agent. Typically, the diluent comprises a fluid (liquid) in which the one or more active agents are soluble. The diluent may be, for example, water, saline solution, or a pH buffer.

In some embodiments of the invention, the container may be a vial suitable for retaining a diluent and the closure may be a vial cap suitable for retaining one or more active agents. Typically, breaking through a portion of the breakable wall by sliding the hollow piston from the default position thereby permits at least some of the one or more active agents retained within the vial cap to fall into and mix with the diluent retained by the vial. Typically, once the breakable wall has been broken, agitation of the container will permit the one or more active agents to dissolve into the diluent. A medical practitioner may extract a portion of the resulting solution from the container by piercing an injection port provided in the vial cap with a needle and drawing the solution into a syringe. Since the portion of the breakable wall broken by the hollow piston remains hingedly attached to the closure, it typically does not interfere with this extraction process.

In alternative embodiments, the container may further comprise a patient delivery mechanism for delivering the contents of the contained into a patient. Such a patient delivery mechanism may be operable without the use of a syringe or needle. This may be necessary in situations where syringes are not readily available, or for use in non-sterile environments. A patient delivery mechanism may comprise a dropper. A dropper may be used for topical, ocular or oral administration of the dissolved one or more active agents to a patient. Alternatively, the patient delivery mechanism may comprise a spray nozzle. A spray nozzle may be used for topical, oral or nasal administration of the dissolved one or more active agents to a patient. The dissolved one or more active agents may, therefore, be administered directly to a patient without the potential for contamination associated with the introduction of an external needle into the container.

In other embodiments, the container may be an intravenous fluid bag suitable for retaining a diluent, the intravenous fluid bag having an inlet, and the closure may be an inlet closure suitable for retaining one or more active agents. Typically, breaking through a portion of the breakable wall by sliding the hollow piston from the default position thereby permits at least some of the one or more active agents retained within the inlet closure to fall into and mix with the diluent retained within the intravenous fluid bag. Typically, the intravenous fluid bag further comprises a patient delivery mechanism, such as a fluid outlet, for administration of the contents of the intravenous fluid bag to a patient. The dissolved one or more active agents may therefore be delivered directly to the patient's bloodstream without contamination.

A fifth aspect of the invention provides a closure for dispensing one or more active agents into a container, the closure comprising a sealed or sealable chamber and an injection port, wherein the closure further comprises an injection port cover positioned on an external surface of the injection port.

The injection port may be retained within an opening of the chamber. The injection port may form a seal across said opening of the chamber. Typically, the injection port is pierceable by a needle. Typically, the injection port is made of a resilient material, for example a plastics material. Typically, the resilient material from which the injection port is made is also pierceable by a needle.

In some embodiments, the injection port comprises a plug configured and dimensioned for an interference fit within the opening of the chamber. In other embodiments, the injection port comprises a membrane configured to seal the opening of the chamber. In further embodiments, the injection port comprises a septum made of plastics material, such as rubber, for example silicone rubber. Typically, when the injection port is retained in the opening of the chamber such that the chamber is sealed from fluid communication with the surroundings, the injection port remains pierceable by a needle such that fluids may be injected into or extracted from said chamber.

Typically, the closure further comprises a breakable wall. Said breakable wall may form a wall of the chamber. The closure may further comprise a hollow piston slidably mounted in a piston guide and comprising an outer wall with an end within the chamber, facing the breakable wall. Typically, the injection port and the breakable wall are aligned with a longitudinal axis of the hollow piston. The injection port may be integral with the hollow piston. Therefore, a straight needle inserted into the chamber through the injection port may extend through the hollow piston, generally parallel to its longitudinal axis, and reach or extend through the breakable wall.

Typically, the injection port cover is provided on an external surface of the injection port. The injection port cover may comprise an adhesive film. Alternatively, the injection port cover may comprise an adhesive tab. Typically, the injection port cover is manually removable. A medical practitioner may, therefore, gain access to the injection port by removing the injection port cover. The injection port cover may be a sterile covering. In such embodiments, the injection port cover ensures that the injection port remains sterile prior to use by the medical practitioner.

It may be that the injection port is provided on the end of the hollow piston which is opposite the end which is within the chamber, facing the breakable wall. Said opposite end is pushed by a user in use to cause the piston to slide within the piston guide and break the breakable wall. It may be that said injection port cover covers the injection port on the said opposite end of the piston. It may be that the closure further comprises a removable cap arranged to cover said end of the hollow piston. It may be that the removable cap is also arranged to cover the external surface of the injection port and the injection port cover. The removable cap may thereby restrict (e.g. prevent) manual depression of the hollow piston (until the cap is removed). Accordingly, the closure is safe to transport as the hollow piston may not be accidentally depressed. The removable cap must typically be removed in order for a user to manually depress the hollow piston by applying a manual force to said opposite end of said hollow piston. The user must therefore typically apply a manual force to the injection port covered by the injection port cover. The injection port cover typically maintains sterility of the injection port while the user depresses the hollow piston. In order to extract the contents of the container once the hollow piston has been deployed, the user must typically remove the injection port cover from the injection port. The removable cap and the injection port cover in combination therefore allow the hollow piston to be safely deployed while maintaining the sterility of the injection port.

The removable cap may be made of a rigid material, for example a rigid plastics material. The removable cap may therefore protect the injection port and the injection port cover.

The removable cap may releasably engage with an external surface of the sealed or sealable chamber to thereby releasably retain said removable cap on the closure. For example, an edge of the removable cap may releasably engage with an edge or a flange of the sealed or sealable chamber to thereby releasably retain said removable cap on the closure. Alternatively, the removable cap may releasably engage with an external surface of the container to thereby retain said removable cap on the container and covering the closure. For example, an edge of the removable cap may releasably engage with an edge or a flange of the container to thereby releasably retain said removable cap on the container and covering the closure. In such embodiments, it may be that once the removable cap has been removed from the closure or the container, manual depression of the hollow piston is no longer restricted (e.g. prevented).

It may be that a release strip is provided between the edge of the removable cap and the external surface of the closure or the container, said release strip releasably connecting said edge of the removable cap to the external surface of the closure or the container. It may be that the release strip is integrally formed with the removable cap and further comprises a pre-weakened or perforated line to facilitate removal of the release strip. It may be that the release strip may be manually removed by peeling said release strip along the pre-weakened or perforated line. It may be that manual removal of said release strip releases the edge of the removable cap from the external surface of the closure of the container, thereby allowing the removable cap to be manually removed.

A sixth aspect of the invention provides a container and a closure according to the fifth aspect of the invention for dispensing one or more active agents into said container, wherein the closure is retained within an opening of the container. Typically, the closure provides a seal for said opening of the container. It may be that the chamber is sealed and retains one or more active agents and the container retains liquid diluent (and is typically sealed by the closure).

A seventh aspect of the invention provides a method of manufacturing a pre-loaded container for use in dispensing one or more active agents comprising the steps of: providing a container body, a closure having a sealed or sealable chamber, an injection port and a hollow piston having at least one ventilation aperture slidable in a piston guide, a solution containing one or more active agents, a diluent, and an inert gas; injecting a portion of the solution containing one or more active agents into the chamber through the injection port; lyophilising the solution in the chamber; sealing the closure by sealing the at least one ventilation aperture, thereby sealing the chamber; injecting a portion of the inert gas into the chamber through the injection port; and adding a portion of the diluent to the container body and sealing the container body with the closure.

Typically, the step of adding a portion of the diluent to the container body and sealing the container body with the closure may occur before or after the steps of injecting a portion of the solution containing one or more active agents into the chamber and/or lyophilising the solution in the chamber and/or injecting a portion of the inert gas into the chamber. In fact, the steps of the method may be performed in any suitable order.

It may be that the container body, the closure, the injection port and the hollow piston are sterilised before use. Alternatively, it may be that all components are sterilised before use.

Typically, the diluent is a fluid into which the one or more active agents is dissolvable. For example, the diluent may be Water for Injection (WFI). Alternatively, the diluent may be saline, a pH buffer, or any other suitable diluent.

Typically, at least one of the one or more active agents comprises a biologic agent. At least one of the one or more active agents may comprise an agent from the following group: a protein, an enzyme, a nucleic acid sequence, a vaccine or an antibiotic. It may be that the one or more active agents are provided in the form of a cake or tablet of lyophilised active agent.

The solution containing one or more active agents may be provided inside a syringe. Typically, the step of injecting a portion of the solution containing one or more active agents into the chamber comprises the steps of first piercing the injection port of the closure with a needle and then injecting the portion of the solution containing one or more active agents from a syringe into the chamber through the needle.

Typically the step of lyophilising the solution containing one or more active agents inside the chamber comprises the steps of: freezing the solution containing one or more active agents; evacuating the surroundings of the closure with the at least one ventilation aperture open; and warming the closure in vacuo such that frozen solvent molecules sublime and escape from the chamber through the at least one ventilation aperture into the surroundings leaving the lyophilised one or more active agents inside the chamber. Once the one or more active agents are lyophilised inside the chamber, the chamber is typically sealed from the surroundings by sealing the at least one ventilation aperture. Typically, the at least one ventilation aperture is sealed by sliding the hollow piston within the chamber from a ventilation position in which the at least one ventilation aperture is open to a sealed position in which the at least ventilation aperture is sealed.

Typically, once the at least one ventilation aperture is sealed, the portion of inert gas is injected into the chamber. The inert gas may comprise any gas which does not react chemically with the one or more active agents. For example, the inert gas may be nitrogen gas. It may be that the inert gas is provided inside a syringe. Typically, the step of injecting a portion of the inert gas into the chamber comprises the steps of first piercing the injection port of the closure with a needle and then injecting the portion of the inert gas into the chamber through the needle.

The portion of inert gas injected into the chamber expands to fill said chamber, relieving any internal vacuum conditions from the chamber. Once the portion of inert gas has been injected into the chamber, the vacuum conditions of the surroundings of the closure are typically lifted. Since the chamber is already filled with one or more lyophilised active agents and the portion of inert gas, there is no pressure difference which could cause air or fluid to be drawn into the chamber from the surroundings (through, for example, the injection port). The chamber and its contents, therefore, remain sealed and sterile.

The method may further comprise the step of providing a sterile covering over the injection port. It may be that the sterile covering comprises an adhesive film. In alternative embodiments, the sterile covering comprises an adhesive tab. In some embodiments, the sterile covering comprises an adhesive label which further seals the closure to the container body.

Since both the solution comprising one or more active agents and the portion of inert gas are typically injected sequentially into the closure through the same injection port, the method of manufacture is straightforward and suited to large-scale mechanisation.

An eighth aspect of the invention provides a pre-loaded container for use in dispensing one or more active agents comprising a container body and a closure according to the first aspect of the invention or a closure according to the third aspect of the invention or a closure according to the fifth aspect of the invention, or a pre-loaded container manufactured according to the method of the seventh aspect of the invention, the container body retaining a portion of diluent and the closure retaining one or more lyophilised active agents, wherein said closure forms a sterile seal across an opening of said container body.

It may be that the container body is a vial and the closure is a vial cap. Said vial may further comprise a patient delivery mechanism. For example, the patient delivery mechanism may be a dropper. Alternatively, the patient delivery mechanism may be a spray nozzle.

In alternative embodiments, the container is an intravenous fluid bag suitable for retaining a diluent, the intravenous fluid bag having an inlet, and the closure is an inlet closure suitable for retaining one or more active agents A ninth aspect of the invention provides a method of using the pre-loaded container according to the eighth aspect of the invention to dispense one or more active agents, the method comprising the steps of: manually sliding the hollow piston from the default position to break through a portion of the breakable wall but not in an area of said breakable wall proximate the gap in the cutting formation; agitating the contents of the pre-loaded container such that the one or more active agents mix with and dissolve into the portion of diluent.

The method may further comprise the steps of removing a covering from an external surface of the injection port; inserting a needle into the container through the injection port; and drawing a portion of a solution resulting from the dissolution of the one or more active agents into the portion of diluent from the container into a syringe through the needle. The method may also further comprise the step of administering a portion of the solution to a patient.

Features disclosed above in relation to any aspect of the invention are optional features of each aspect of the invention.

DESCRIPTION OF THE DRAWINGS

An example embodiment of the present invention will now be illustrated with reference to the following Figures in which:

FIG. 1 shows a cross section through a vial and a vial closure;

FIG. 2 shows a cross section through the vial of FIG. 1;

FIG. 3 shows a cross section through the vial closure of FIG. 1;

DETAILED DESCRIPTION OF AN EXAMPLE EMBODIMENT

Figures 4, 5:
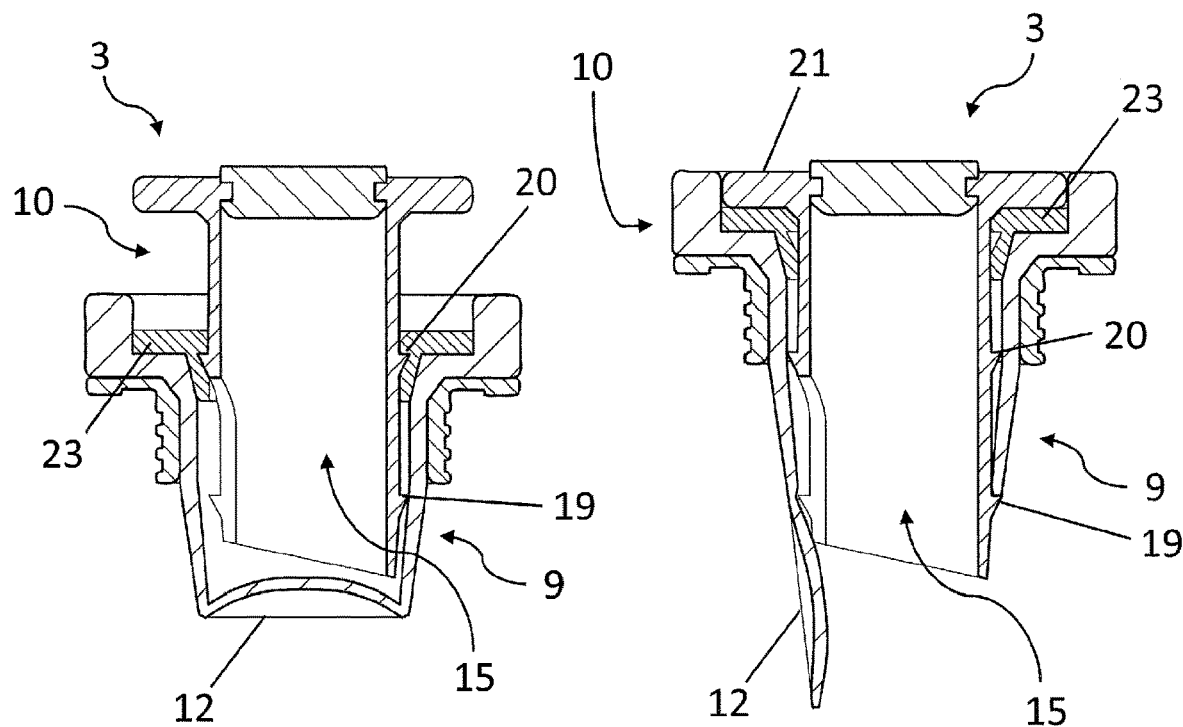
FIG. 4 shows a cross section through the vial closure of FIG. 3 in an alternative arrangement.
FIG. 5 shows a cross section through the vial closure of FIG. 3 in a further alternative arrangement.

A container 1 for use in dispensing one or more active agents as shown in FIG. 1 comprises a vial 2 and a vial closure 3. The vial 2, as shown in FIG. 2, comprises a vial body 4 comprising a generally cylindrical side wall 5 extending upwards from a generally circular base 6. A generally cylindrical opening 7 is provided opposite said circular base 6. Together the base 6 and the cylindrical side wall 7 define an internal vial chamber 8. The vial body 4 is made from glass or plastics, or any other suitable material.

The vial closure 3, as shown in FIG. 3, comprises a vial closure body 9 and a vial closure lid 10. The vial closure body 9 comprises a generally cylindrical closure wall 11 dimensioned and configured for an interference fit within the opening 7 of the vial body 4 when the vial closure 3 is fully inserted into said opening 7. The closure wall 11 is typically made of a resilient plastics material. A generally circular closure base 12 extends across the end of the vial closure body 9 which is inserted into the opening 7 of the vial body 4 when in use. The vial closure base 12 is made of a pierceable material such as a plastics material or glass (functioning as the breakable wall). A chamber 15 is defined by the cylindrical closure wall 11 and circular closure base 12.

The vial closure lid 10 comprises a generally cylindrical lid wall 13 extending from a generally circular lid cover 14. The lid wall 13 is made of a rigid plastics material. The lid cover 14 is made of a resilient plastics material, for example rubber. The lid wall 13 is dimensioned and configured to fit within the chamber 15 formed by the closure wall 11 and closure base 12. The lid wall 13 functions as the hollow piston (and as the outer wall of the hollow piston). The base edge 17 of the lid wall is at the end of the outer wall of the piston facing the breakable wall.

A gap 16 is provided in the lid wall 13. The rest of the base edge 17 functions as the cutting formation and may or may not be sharp, depending on the strength of the breakable wall. The base edge 17 of the lid wall is sloping opposite the lid cover and protrudes further towards the breakable wall on the side opposite the gap. The sloping base edge 17 of the lid wall 13 is adjacent the closure base 12 when the vial closure lid 10 is inserted into the closure chamber 15. An injection port 18 is provided in the centre of the lid cover 14 such that a needle may be removably inserted through said injection port 18 into the chamber 15 formed by the vial closure body 9 when the chamber is covered by the vial closure lid 10. The injection port 18 comprises a rubber septum.

The generally cylindrical lid wall 13 comprises an internal surface 13A and an external surface 13B. Three generally circular flanged edges extend from the external surface 13B of the lid wall 13 around the circumference of said lid wall 13. The first flanged edge 19 is positioned adjacent to and set back from the sloping base edge 17 of the lid wall. The second flanged edge 20 is positioned approximately midway between the sloping base edge 17 of the lid wall 13 and the lid cover 14. The third flanged edge 21 is positioned adjacent to the lid cover 14. The third flanged edge 21 extends substantially further outwards from the external surface 13B of the lid wall 13 than the first 19 and second 20 flanged edges. The third flanged edge 21 is configured to engage with a top surface 22 of the closure body 9 when the lid 10 is inserted into the closure chamber 15.

The generally cylindrical closure wall 11 also comprises an internal surface 11A and an external surface 11B. The internal surface 11A of the closure wall 11 comprises a flexible seal 23 adjacent to the end of the closure wall 11 which is proximate the lid cover 14 when the vial closure lid 10 is inserted into the closure chamber 15. The flexible seal 23 is made from a resilient plastics material, for example rubber. The flexible seal and in some embodiments the internal surface 11 of the closure wall 11, functions as the piston guide. The hollow piston formed by lid wall 13 and its base edge 17 is slidably mounted in the piston guide. The flexible seal 23 is positioned, dimensioned and configured to be releasably engageable with the first 19 and second 20 flanged edges of the lid wall 13 to releasably retain the vial closure lid 10 in two possible positions such that the vial closure lid 10 is moveable into, out of and between said two positions. In the first position illustrated in FIG. 3, the first flanged edge 19 engages the flexible seal 23. In such a position, the vial closure lid 10 is held apart from the vial closure body 9 such that the aperture 16 in the lid wall 13 permits fluid communication between the closure chamber 15 and the surroundings. In the second position illustrated in FIG. 4, the second flanged edge 20 engages with the flexible seal 23. In such a position, the vial closure lid 10 has been inserted into the closure chamber 15 such that the aperture 16 is covered by the closure wall 11 and no fluid communication between the closure recess 15 and the surroundings is permitted. The pierceable closure base 12 remains intact in both the first and second positions.

The vial closure seal is also moveable from the second position illustrated in FIG. 4 (where the closure chamber 15 is sealed from the surroundings and the pierceable vial closure base 12 is intact) to a third position illustrated in FIG. 5 where the third flanged edge 21 of the lid wall 13 engages with the top surface 22 of the closure body 9. In such a third position, the sloping base edge 17 of the lid wall 13 pierces the pierceable closure base 12 and extends beyond it such that the previously sealed closure chamber 15 is brought into fluid communication with the surroundings. The placement of the aperture 16 ensures that only a portion of the circumference of the pierceable base 12 is cut when the vial closure lid 10 is held in the third position. The aperture 16 therefore performs a dual role in both permitting fluid communication between the closure chamber 15 and the surroundings in the first position and also by ensuring that only a portion of the circumference of the pierceable base 12 is cut when the vial closure lid 10 is held in the third position, while retaining the mechanical strength and integrity of the lid wall 13 and thus the reliability of the vial closure 3.

When the vial closure lid 10 is retained in the third position, the third flanged edge 21 of the lid wall 13 engages with the top surface 22 of the vial closure body 9. The first flanged edge 19 also engages with a newly-formed bottom edge of the closure wall 11 (formed by the cut through the pierceable base 12). The vial closure lid 10 is, therefore, locked into the third position, since the combined action of the first 19 and third 21 flanged edges prevents further movement of the vial closure lid 10 into or out of the vial closure chamber 15.

In use, the circumference of the pierceable base 12 is not cut in an area proximate the gap 16 in the lid wall 13. The pierceable base 12, therefore, remains hingedly attached to the vial closure wall 11 in the area proximate the gap 16 in the lid wall 13. The vial closure lid 10 therefore acts as a piston 10, cutting through the pierceable wall 12, and bringing the closure chamber 15 into fluid communication with the vial chamber 8.

Figures 6, 7:
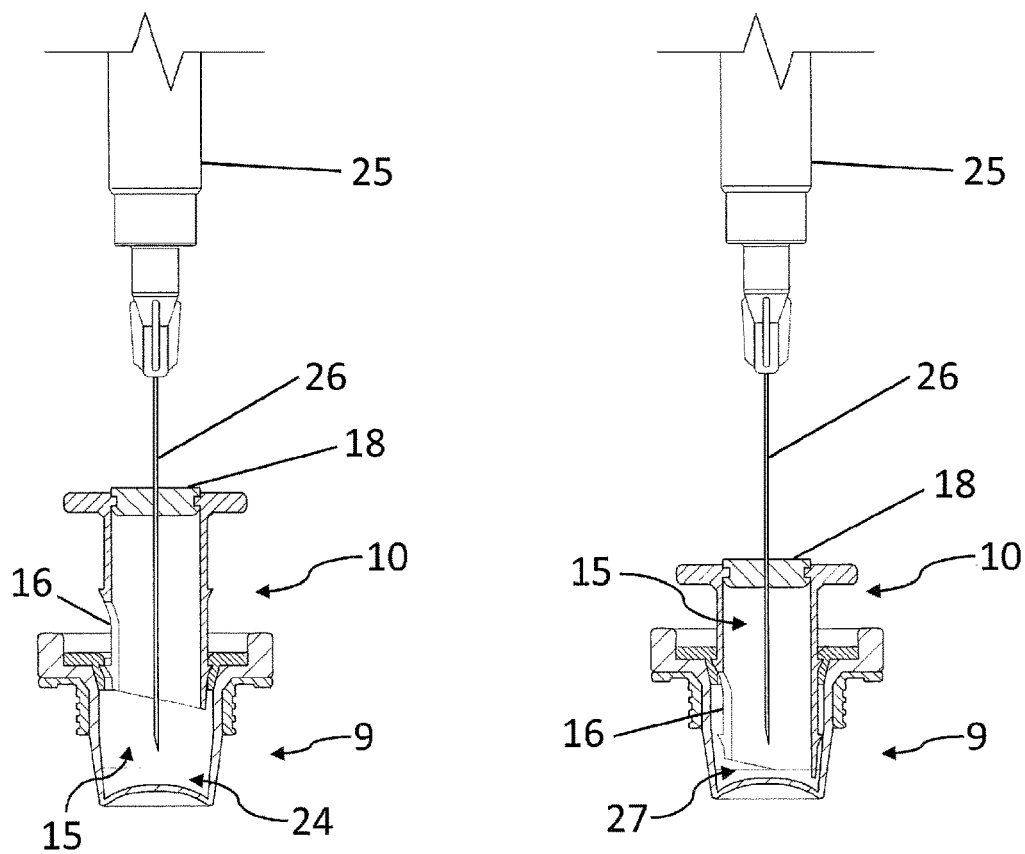
FIG. 6 shows a cross section through a needle penetrating the vial closure of FIG. 3 retaining one or more active agents.
FIG. 7 shows a cross section through a needle penetrating the vial closure of FIG. 4 retaining one or more active agents.
Figure 8:
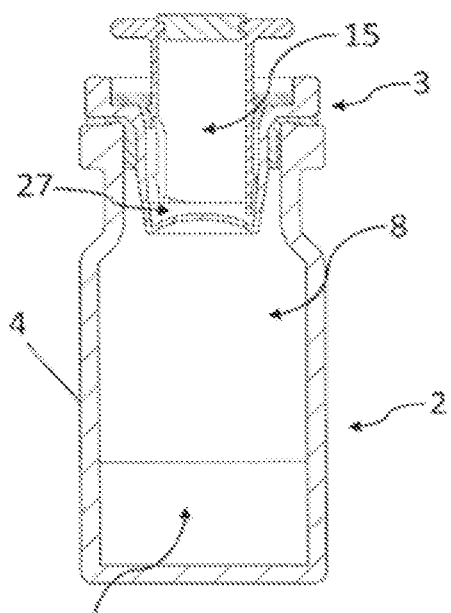
FIG. 8 shows a cross section of a vial retaining a diluent and a vial closure retaining one or more active agents.

The method of manufacturing the pre-loaded container ready for use in dispensing one or more active agents is illustrated in FIGS. 6, 7 and 8. The vial closure body 9 and vial closure lid 10 are sterilised and then placed in the first position (as shown in FIG. 6), where the first flanged edge 19 engages with the flexible seal 22. The gap 16 in the lid wall 13 is uncovered. A solution is prepared comprising one or more active agents. A syringe 25 is used to inject a portion of the solution 24 containing one or more active agents into the chamber 15 formed between the vial closure body 9 and vial closure lid 10 by piercing the injection port 18 with a needle 26 (as illustrated in FIG. 6). The one or more active agents are then lyophilised within the chamber. The lyophilisation step comprises the steps of freezing the solution 24 within the recess and then heating the frozen solution under vacuum conditions such that the solvent sublimes. Solvent molecules are able to escape from the chamber 15 to the surroundings through the gap 16. The lyophilised one or more active agents 27 remain inside the chamber 15. The vial closure lid 10 is then moved either manually or mechanically to the second position (shown in FIG. 4), where the second flanged 20 edge engages with the flexible seal 23. The gap 16 in the lid wall 13 is now covered such that the chamber 15 is no longer ventilated. An inert gas, such as nitrogen gas, is then injected into the chamber 15 from a syringe 25 by piercing the injection port with a needle 26 (FIG. 7). The inert gas fills the remaining space inside the chamber 15 so that air or other fluids are not drawn into the chamber 15 through the injection port 15 as the surrounding vacuum conditions are removed. This ensures the contents of the chamber 15 remain sterile. The advantage provided by lyophilisation is that the one or more active agents 27 retained in the chamber 15 are not structurally altered but are more stable than in solution. A portion of a suitable diluent 28 is then provided inside the chamber 8 of the sterilised vial body 4 and the filled vial closure 3 (comprising the vial closure body 9, the vial closure lid 10 in the second position and the lyophilised one or more active agents 27 retained within the closure chamber 15) is inserted into the opening 7 of the vial body 4 with an interference fit such that the opening 7 is sealed, as illustrated in FIG. 8. This ensures that the diluent 28 and the one or more active agents 27 are sealed from external contaminants and from one another.

Figure 9:
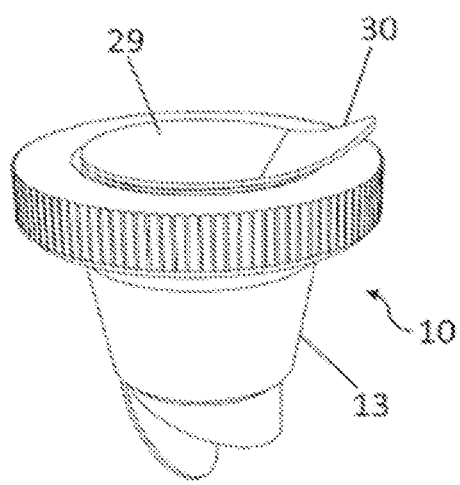
FIG. 9 shows a perspective view of a vial closure with an injection port and a sterile covering.
Figure 10:
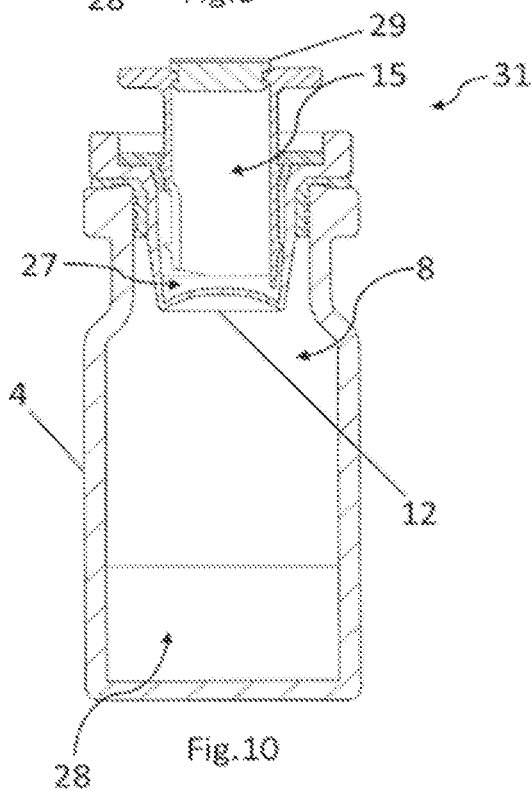
FIG. 10 shows a cross section of a vial retaining a diluent and a vial closure retaining one or more active agents with a sterile covering.
Figure 11:
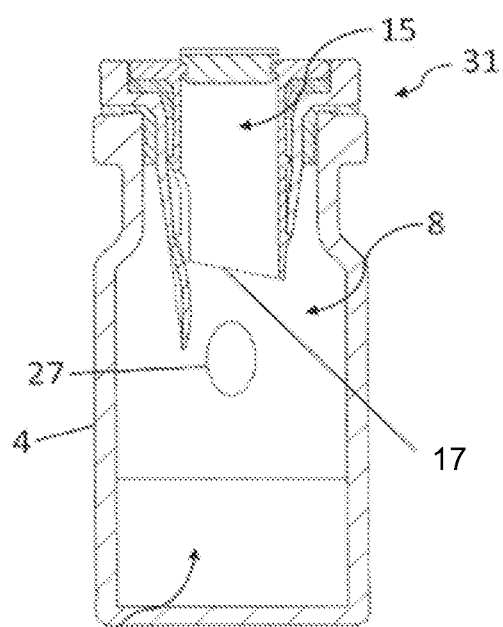
FIG. 11 shows a cross section of a vial retaining a diluent and one or more active agents falling from a vial closure into the diluent.

As illustrated in FIG. 9, a removable sterile covering 29 is provided on top of the injection port 18 of the vial closure lid 10. The sterile covering 29 is made of a plastics material and is attached to the vial closure lid 10 by means of an adhesive. A portion of the sterile covering, a tab 30, is not coated in adhesive, to facilitate subsequent removal of said sterile covering 29 by a medical practitioner during use.

A preloaded container 31 so manufactured can be transported or stored safely within a refrigerator, or according to the recommended storage conditions for the diluent 28 and the one or more active agents 27, to await use.

Figure 12:
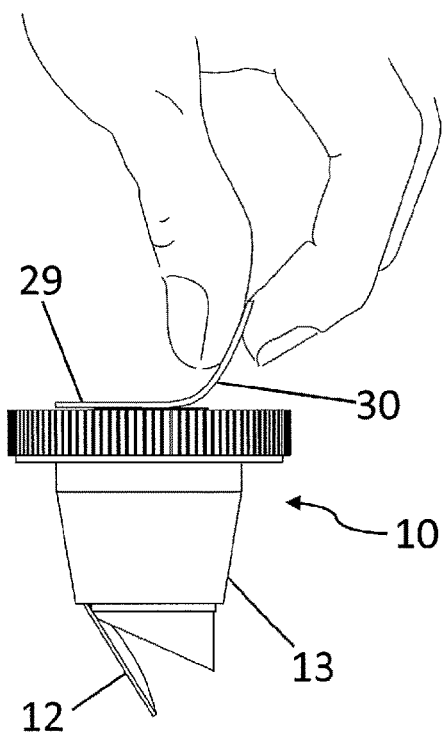
FIG. 12 shows a side view of a medical practitioner removing a sterile covering from a vial closure.
Figure 13:
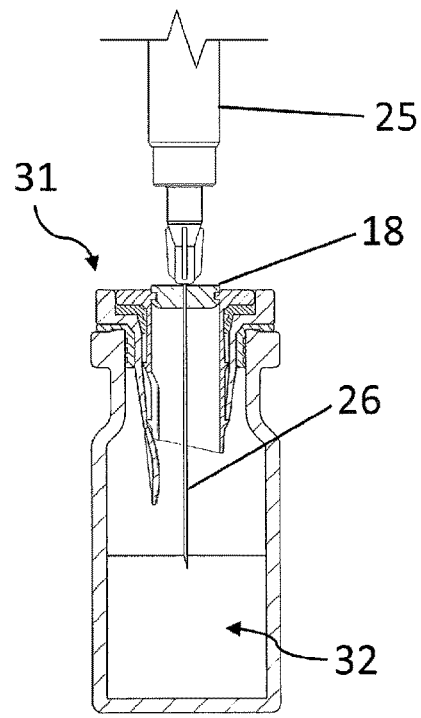
FIG. 13 shows a cross section of a vial retaining a solution and a needle penetrating a vial closure.

The use of a pre-loaded container 31 for dispensing one or more active agents 27 so manufactured is illustrated in FIGS. 10, 11, 12 and 13. A medical practitioner receives the pre-loaded container 31 in a first state illustrated by FIG. 10, where the vial chamber 8 retains a diluent 28, the closure chamber 15 retains one or more lyophilised active agents 27, the vial closure 3 seals the opening 7 to the vial body 4, and the vial closure lid 10 is in its second position such that the closure chamber 15 is sealed from the surroundings while the pierceable closure base 12 is intact. When the pre-loaded container 31 is ready to be used, the medical practitioner manually depresses the top surface of the vial closure lid 10, moving the vial closure lid 10 to the third position where the third external flange 21 engages with the top surface 22 of the vial closure body 9. The vial closure lid 10 acts like a piston, cutting through a portion of the circumference of the pierceable closure base 12 and bringing the closure chamber 15 into fluid communication with the vial chamber 8 (see FIG. 11). The lyophilised one or more active agents 27 fall into the diluent 28. Agitation of the contents of the pre-loaded container 31 ensures thorough dissolution of the one or more active agents 27 into the diluent 28. As illustrated in FIG. 12, the medical practitioner then removes the sterile covering 29 provided on top of the injection port 18 by peeling back said covering 29 by means of the non-adhered tab 30. The solution 32, resulting from the dissolution of the one or more active agents 27 into the diluent 28, is extracted from the pre-loaded container 31 for administration to a patient using a syringe 25 by piercing the injection port 18 with a needle 26 (FIG. 13). The solution 32 is drawn into the syringe 25. The closure base 12 remains hingedly attached to the closure wall 11 and does not fall into the solution 32 and, therefore, does not interfere with the syringe 25.

Figure 14:
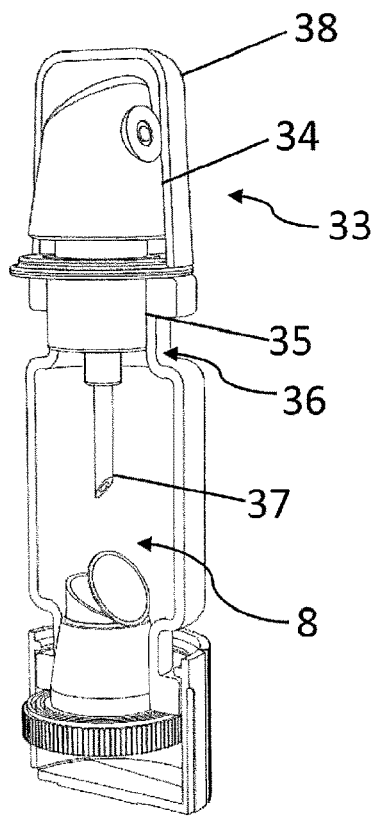
FIG. 14 shows a perspective view of a cut through a vial with a vial closure and a nozzle.
Figure 15:
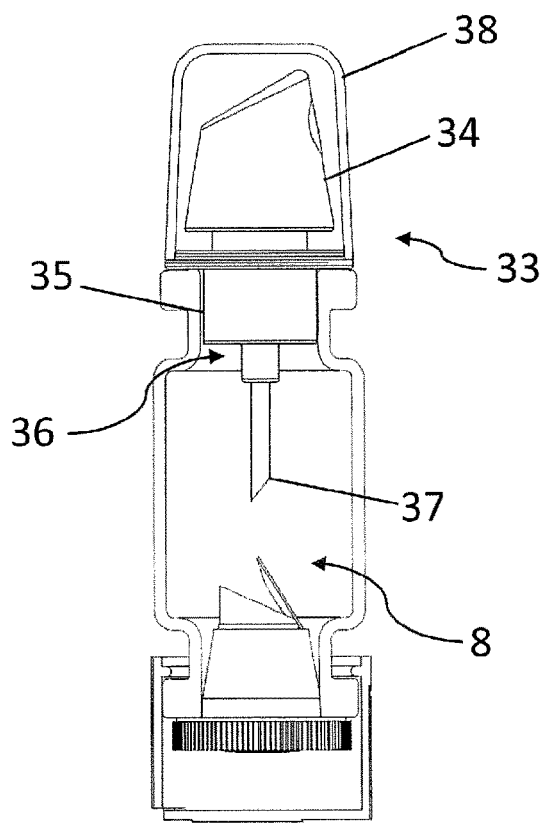
FIG. 15 shows a side view of the vial with the vial closure and the nozzle of FIG. 14.

In variations of the invention, the vial body further comprises a patient delivery mechanism. In one such variation, for example, as shown in FIGS. 14 and 15, the generally circular base 6 of the vial body 4 of the container 1 as described previously is replaced with a pump-action nozzle 33. The nozzle comprises a nozzle head 34 extending from a nozzle seal 35. The nozzle seal 35 is dimensioned and configured for an interference fit within a second opening 36 of the vial body 4. A nozzle tube 37 extends between the nozzle head 34 and the vial chamber 8, through the nozzle seal 35, such that the nozzle head 34 is in fluid communication with the vial chamber 8. A removable lid 38 is provided over the nozzle head 34. When in use, once the one or more active agents 27 have been released into the vial chamber 8 and combined with the diluent 28, the resulting solution 32 may be administered directly to a patient by means of the pump-action nozzle 33, once the lid 38 has been removed. This removes the possibility of external contamination of the solution by the introduction of a needle through the injection port. A pump-action nozzle 33 is suitable for, for example, topical or nasal administration of the one or more active agents.

Figure 16:
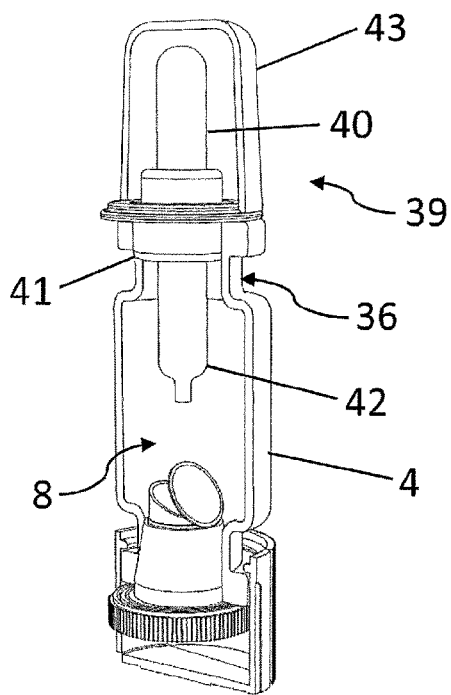
FIG. 16 shows a perspective view of a cut through a vial with a vial closure and a dropper.
Figure 17:
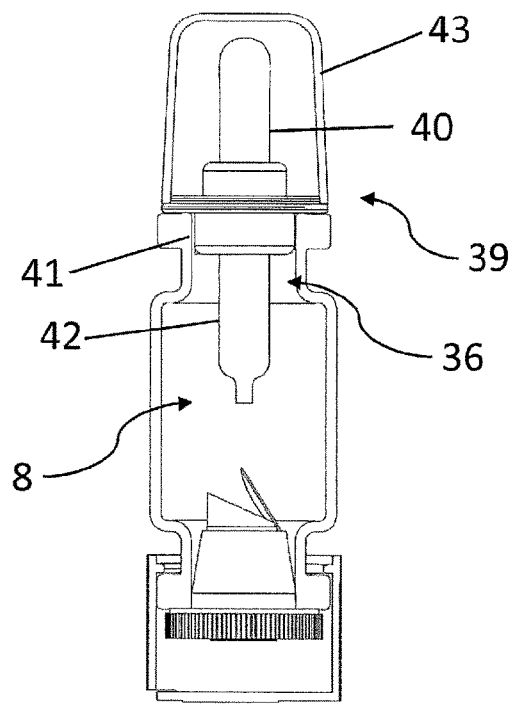
FIG. 17 shows a side view of the vial with the vial closure and the dropper of FIG. 16.

In another variation, as shown in FIGS. 16 and 17, the generally circular base 6 of the vial body 4 of the container 1 as described previously is replaced with a dropper 39. The dropper 39 comprises a dropper bulb 40 extending from a dropper seal 41. The dropper seal 41 is dimensioned and configured for an interference fit within a second opening 36 of the vial body 4. A dropper tube 42 extends between the dropper bulb 40 and the vial chamber 8, through the dropper seal 41, such that the dropper bulb 40 and dropper tube 42 are in fluid communication with the vial chamber 8. A removable lid 43 is provided over the dropper bulb 40. When in use, once the one or more active agents 27 have been released into the vial chamber 8 and combined with the diluent 28, the resulting solution 32 may be administered directly to a patient by means of the dropper 39 once the lid 43 has been removed. This removes the possibility of external contamination of the solution by the introduction of a needle through the injection port. A dropper 39 is suitable for, for example, topical, oral or ocular administration of the one or more active agents.

Figure 18:
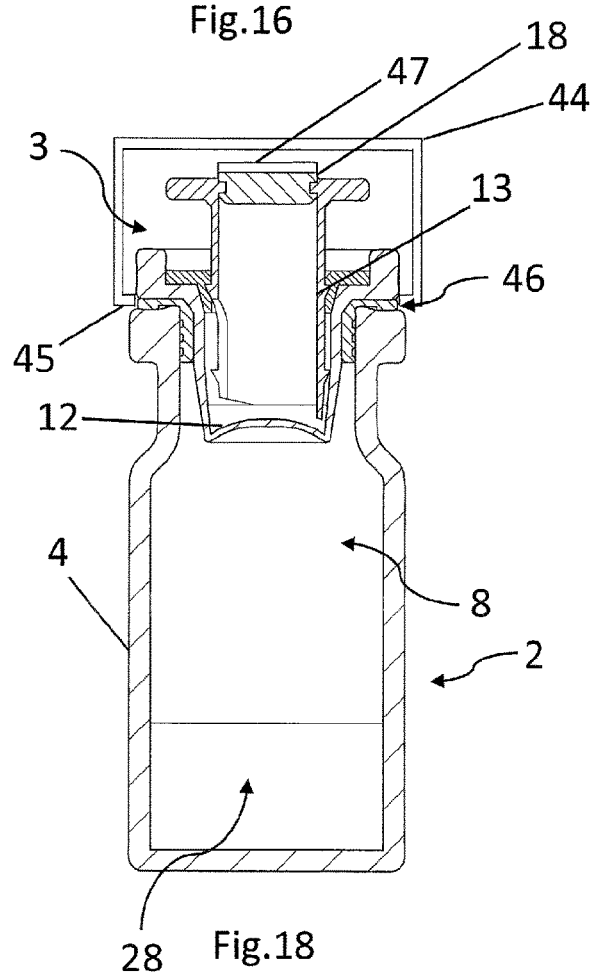
FIG. 18 shows a cross section through a vial with a vial closure and a removable cap.

FIG. 18 shows a variation of the invention which further includes a removable cap 44 positioned over the vial closure 3. A flange 45 of the removable cap 44 engages with a flange 46 of the vial 2, thereby retaining the removable cap over the vial closure 3. The removable cap 44 may for example be formed by crimping. The removable cap 44 protects the vial closure 3. The removable cap 44 restricts depression of the piston 13. The removable cap 44 therefore reduces the likelihood that the piston 13 is inadvertently depressed (resulting in breaking of the breakable wall 12). The injection port 18 is, in addition, covered by adhesive injection port cover 47, underneath the cap. Adhesive injection port cover 47 protects injection port 18 during manual depression of the piston 13 once removable cap 44 has been removed. Adhesive injection port cover 47 ensures that injection port 18 remains sterile. Removal of adhesive injection port cover 47 allows a user to access the sterile injection port 18.

The removable cap 44 is made of a plastics material. The plastics material is flexible enough that the removable cap 44 may be deformed in order to remove said removable cap 44 from the closure 3. However, the plastics material is also rigid enough that the removable cap 44 is typically retained on the closure 3 unless deliberately removed. The removable cap 44 may also be releasably connected to the closure 3 by other means. For example, the removable cap 44 may be sealed to the vial closure 3 by way of an adhesive, such as an adhesive strip, or by way of a removable connecting strip integrally formed with the removable cap 44.

Figure 19:
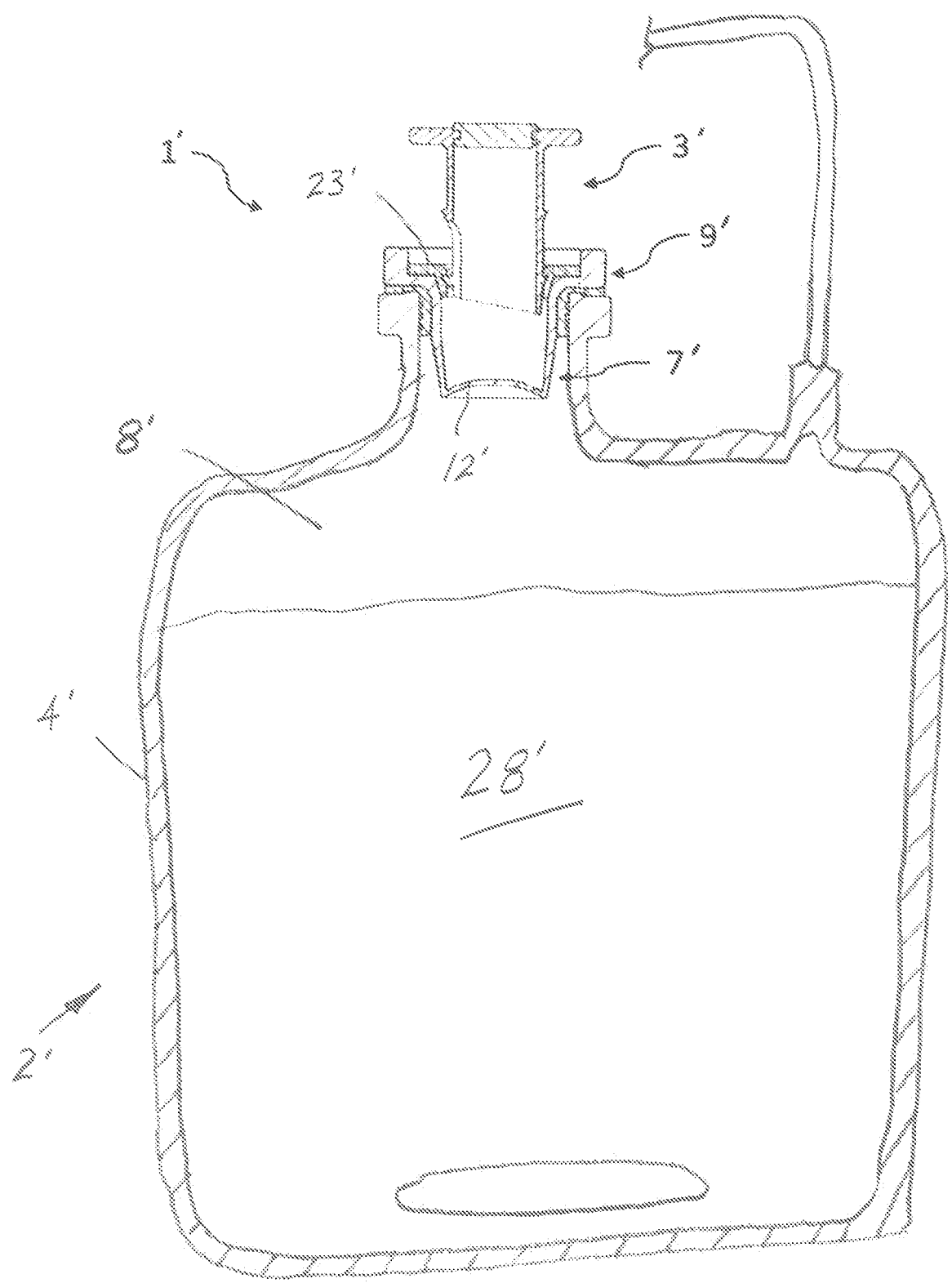
FIG. 19 shows a cross section through a closure and intravenous bag.

FIG. 19 shows a container 1' where the closure 3' is received in an opening 7' of the container 2' which is shown as an intravenous (IV) bag 4'. The IV bag 4' is illustrated in inverted fashion before it is hung from a carrier or support (not shown) as is well known in the art. The IV bag encloses an internal chamber 8' that is closed by the closure 3' that includes a closure body 9'. Flexible seal 23' receives the closure 3' so that in the same manner as described in the earlier embodiments, a pierceable closure base 12' is sealed from the chamber 81 when the closure base 12' is intact, and when the base is pierced, one or more active agents fall into the diluent 28' where the agents are dissolved into the diluent.

Further modifications and variations may be made within the scope of the invention herein disclosed.

The invention claimed is:

1. A closure for dispensing one or more active agents into a container, the closure comprising: a sealed or sealable chamber having a breakable wall, a hollow piston slidably mounted in a piston guide, said hollow piston comprising an outer wall, said outer wall having an end in the chamber and at least one ventilation aperture, said end having a cutting formation having a gap provided therein, and when the closure is inserted in an opening of the container, said hollow piston being slidable in the piston guide between a ventilation position in which the at least one ventilation aperture is dimensioned to allow ventilation of the chamber which holds the active agents and a sealed position in which the at least one ventilation aperture is sealed to prevent ventilation of the chamber and a deployed position in which the cutting formation has broken through at least a portion of the breakable wall, wherein the outer wall has a retaining formation which engages with the piston guide to releasably resist sliding of the hollow piston between the ventilation position and the sealed position and the deployed position.

2. The closure according to claim 1, wherein the piston guide comprises a locating formation engageable with the retaining formation of the outer wall.

3. The closure according to claim 2, wherein the locating formation comprises at least one flanged edge portion engageable with the retaining formation of the outer wall.

4. The closure according to claim 1, wherein the gap in the cutting formation is formed by the at least one ventilation aperture.

5. The closure according to claim 1, wherein the breakable wall is not broken in an area proximate the gap in the cutting formation when the hollow piston is in the deployed position.

6. A container and a closure according to claim 1, for dispensing one or more active agents into said container, wherein the closure is retained within an opening of the container and the closure provides a seal for said opening of the container.

7. A pre-loaded container for use in dispensing one or more active agents comprising a container body and a closure according to claim 1.

8. The pre-loaded container according to claim 7, wherein the container body is a vial and the closure is a vial cap.

9. The pre-loaded container according to claim 8, wherein the vial further comprises a patient delivery mechanism.

10. The pre-loaded container according to claim 9, wherein the patient delivery mechanism is a dropper or a spray nozzle.

11. The pre-loaded container according to claim 7, wherein the container is an intravenous fluid bag suitable for retaining a diluent, the intravenous fluid bag having an inlet, and the closure is an inlet closure suitable for retaining one or more active agents.

12. A method of using the pre-loaded container according to claim 7, to dispense one or more active agents, the method comprising the steps of: manually sliding the hollow piston from the default position to break through a portion of the breakable wall but in such a way that not all of the breakable wall is severed by the cutting formation; agitating the contents of the pre-loaded container such that the one or more active agents mix with and dissolve into the portion of diluent.

13. The method according to claim 12, further comprising the steps of removing a covering from an external surface of an injection port; inserting a needle into the container through the injection port; and drawing a portion of a solution resulting from the dissolution of the one or more active agents into the portion of diluent from the container into a syringe through the needle.

14. The method according to claim 13, further comprising the step of administering a portion of the solution to a patient.

* * * * *